United States Patent

Cassinelli et al.

Patent Number: 4,942,155
Date of Patent: Jul. 17, 1990

[54] BIOSYNTHETIC ANTHRACYCLINES RELATED TO DAUNORUBICIN

[75] Inventors: Giuseppe Cassinelli, Voghera; Arpad Grein, Milan; Sergio Merli, Bernareggio Mi; Giovanni Rivola, Milan, all of Italy

[73] Assignee: Farmitalia Carlo Erba S.p.A., Milan, Italy

[21] Appl. No.: 23,390

[22] Filed: Mar. 9, 1987

[30] Foreign Application Priority Data

Mar. 13, 1986 [GB] United Kingdom ............... 8606204

[51] Int. Cl.$^5$ .......................................... C07H 15/252
[52] U.S. Cl. ...................................... 514/34; 514/183; 514/270; 514/908; 536/6.4; 540/468
[58] Field of Search ............... 540/552, 468; 514/183, 514/43, 49, 50, 34, 270, 908; 536/24, 6.4

[56] References Cited

PUBLICATIONS

Oki et al., Chem. Abst., vol. 95, 40852x (1981), eq. EP-26849.
Umezawa et al., Chem. Abst. 107-5725c (1987), eq. EP-206138.
Cassinelli et al., Chem. Abst., 100-50041t (1984).
Ganapathi et al., Chem. Abst., 102-249n (1985).
Krishan et al., Chem. Abst., 104-218544t (1986).
Cassinelli et al., CA 108-110869w (1988).
Komiyama et al., J. of Antibiotics, vol. 30, No. 7, p. 619 (1977).
Takahashi et al., J. of Antibiotics, vol. 30, No. 7, p. 622 (1977).

Primary Examiner—Cecilia Shen
Attorney, Agent, or Firm—Oblon, Fisher, Spivak, McClelland, Maier & Neustadt

[57] ABSTRACT

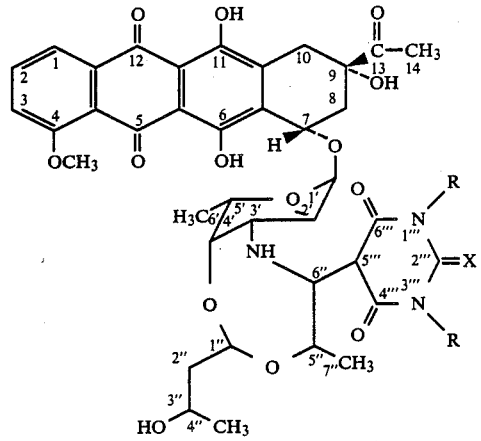

I = FCE 24366: R = CH$_3$; X = O

II = FCE 24367: R = H; X = S are prepared by a biosynthetic process based on the addition of sodium salt of 1,3-N,N-dimethylbarbituric acid and 2-thiobarbituric acid respectively during the fermentation process of different micro-organisms such as *Streptomyces peucetius* and its mutants.

The novel compounds are provided with good antibacterial and antitumour activity.

3 Claims, No Drawings

BIOSYNTHETIC ANTHRACYCLINES RELATED TO DAUNORUBICIN

The invention relates to novel biosynthetic anthacycline antibiotics containing daunorubicin in their molecule; to their production and to pharmaceutical preparation containing them.

The new anthracyclines, hereinafter referred to as FCE 24366 and FCE 24367, are useful as antitumor agents in experimental animals and are also effective gram positive and gram negative bacteria. They have the formula:

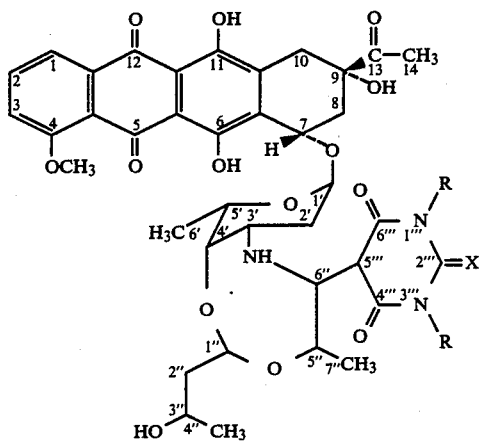

wherein R represents a methyl group and X is an oxygen atom (FCE 24366), or R represents hydrogen and X is a sulphur atom (FCE 24367).

The anthracycline glycosides of the invention are prepared by a process which comprises culturing under aerobic conditions a strain of *Streptomyces peucetius* or of a mutant thereof in an aqueous nutrient medium containing an assimilable source of nitrogen, an assimilable source of carbon, mineral salts and 1,3-N,N-dimethylbarbituric or 2-thiobarbituric acid or an alkali metal or alkaline earth metal salt thereof; and recovering the anthracycline glycoside according to the invention from the culture medium.

The invention thus also relates to a biosynthetic process for the production of FCE 24366 and FCE 24367 based on the addition of sodium salt of 1,3-N-N-dimethylbarbituric acid and 2-thio-barbituric acid respectively during the fermentation of the strain of *Streptomyces peucetius* or of a mutant thereof. For example, a strain of *Streptomyces peucetius* var. carneus, *Streptomyces peucetius* var. carminatus or *Streptomyces peucetius* var. caesius may be cultured. Preferred are *Streptomyces peucetius* strain ATCC 29050, and its mutants: *S. peucetius* var. carneus, strain ATCC 21354, *S. peucetius* var. carminatus, strain ATCC 31502, and *S. peucetius* var. caesius, strain ATCC 27952. The FCE 24366 and FCE 24367 can be obtained by recovery from the fermentation broths, concentration from crude solution and purification. The invention includes within its scope the FCE 24366 and FCE 24367 in the form of crude concentrates, in the pure form as isolated from the crude concentrates and in the form of pharmaceutical compositions with a pharmaceutically acceptable diluent or carrier. A therapeutically effective amount of FCE 24366 or FCE 24367 can be combined with the diluent or carrier. A therapeutically effective amount of FCE 24366 or FCE 24367 is administered to a patient when the compounds are used, for example as an antibiotic or an anti-tumor agent.

On the basis of the proposed unique structural feature, shown in Scheme 1 below, FCE 24366 and FCE 24367 can be considered two novel trisaccharides related to daunorubicin, incorporating a moiety of 1,3-N,N-dimethylbarbituric acid and 2-thiobarbituric acid respectively.

An analogue incorporating barbituric acid, FCE 21424, has been previously described in our Belgian Patent No. 896190 (July 18, 1983) and some trisaccharide-like daunorubicin analogues, such as baumycins $A_1$, $A_2$, $B_1$ and $B_2$ have been reported (The Journal of Antibiotics 30, 619 and 622, 1977). However, chemical and physical properties of FCE 24366 and FCE 24367 differentiate them from all the previously described anthracycline antibiotics.

Fermentation Process

The production is carried out by the usual, well known methods and consists in culturing the microorganisms in a previously sterilized liquid culture medium under aerobic conditions at a temperature ranging from 25° C. to 37° C. (preferably at 28° C.) over a period of time varying from 3 to 7 days (preferably 5 days) and at a pH value which initially is from 6.5 to 7.0 and at the end of the fermentation process ranges from 6.6 to 8.0.

The culture medium consists of a carbon and a nitrogen source as well as of mineral salts.

The carbon source may, for example, be starch, dextrin, glucose, glycerin, mannite, maltose, corn steep liquor, distillers soluble, soybean oil or soybean meal. The nitrogen source, besides the above mentioned complex substances containing nitrogen, may be for example dry yeast, meat peptone or casein. Good results are even obtained by using ammonium salts such as ammonium nitrate, ammonium sulphates, ammonium phosphates. The mineral salts useful for the production may vary according to the medium employed. In a medium containing complex substances such as various meals and fermentation residues, the addition of calcium carbonate and sodium or potassium phosphate has been proved useful. In media containing glucose, or ammonium salts, much higher levels of mineral salts such as potassium, sodium or calcium salts, and additions of microelements like iron, zinc, copper, magnesium and manganese salts are needed. Barbituric acids, as sodium salts, are added in the second or third day of the fermentation.

The fermentation may be carried out in Erlenmeyer flasks or in laboratory as well as in industrial fermenters of various capacities.

Analytical Methods

When samples of fermentation broths and crude mixtures are subjected to thin layer chromatography (TLC) using as eluent a mixture of chloroform:methanol:toluene 7:3:3 (by volume), FCE 24366 and FCE 24367 are found to occur at Rf medium value of 0.65 and 0.60 respectively together with other anthracycline-like constituents at different Rf values.

A quantitative estimation of the total anthracycline-like constituents present in the fermentation broths can be performed by the following method.

To a sample of broth, adjusted at pH 7.6, two volumes of a 9:1 chloroform:methanol mixture are added and the resulting mixture is sonicated for 1 minute at room temperature. On a sample of the organic extract, diluted with methanol, the total content of the anthracycline-like constituents can be spectrophotometrically determined at 495 nm.

When a sample of the same organic extract, is subjected to a TLC analysis, using the above mentioned eluting system, spectrophotometric determinations of FCE 24366 and FCE 24367 at 496 nm, can be performed by scraping off and eluting with a 4:1 chloroform:methanol mixture the corresponding red coloured zones.

Isolation Procedure

After the fermentation is completed, the new anthacyclines FCE 24366 and FCE 24367 are mainly found in the mycelia which are separated from the fermentation liquors by filtration at pH 7.5 with the aid of diatomaceus earth.

The mycelia cake is extracted with a mixture of a water-miscible organic solvent such as acetone, dioxane, methanol and other lower alcohols; preferentially acetone is employed. The mycelial extracts are collected and concentrated under reduced pressure. The aqueous concentrate is extracted at pH 7.5 with a water-immiscible organic solvent such as n-butanol, methylisobutylketone, chloroform, dichloromethane, ethyl acetate; preferentially ethyl acetate is employed. From the organic extracts, dried with anhydrous sodium sulphate and concentrated under reduced pressure, crude FCE 24366 or FCE 24367 can be precipitated by addition of a five-fold volume of n-hexane.

Purification Procedure

Purification of FCE 24366 or FCE 24367 can be achieved by using silica gel dry column chromatography. A solution of crude FCE 24366 or FCE 24367 in a 7:3:3 chloroform:methanol:toluene mixture is subjected to silica-gel dry column chromatography using the above mentioned mixture as eluting solvent. From the selected fractions, monitored by TLC, after concentration in vacuo to a small volume, precipitation with n-hexane and crystallization from ethyl acetate, pure FCE 24366 or FCE 24367 are obtained.

Chemical and Physical Properties

The novel anthracycline antibiotics FCE 24366 and FCE 24367, obtained as fine red crystalline needles, are soluble in acetone, dioxane, N,N-dimethylformamide, N,N-dimethylsulfoxide, slightly soluble in chloroform, dichloromethane, ethyl acetate, lower alcohols, but barely soluble or insoluble in ethyl ether, n-hexane, petroleum ether and water. The novel anthracyclines are unstable in acidic media. The physico-chemical properties and spectroscopic data of FCE 24366 and FCE 24367 are summarized in Tables 1, 2 and 3.

TABLE 1

Chemical and physical properties of FCE 24366 and FCE 24367

| Properties | FCE 24366 | FCE 24367 |
|---|---|---|
| Melting point | 195°–196° C. (dec.) | 210°–211° C. (dec.) |
| U.V. and visible spectrum $\lambda_{Max}^{MeOH}$ | 234, 254, 290, 480, 496 and 530 nm | 234, 254, 290, 480, 496 and 530 nm |
| $E_{1\,cm}^{1\%}$ | 500, 425, 110, 144, 146 and 85 | 450, 385, 90, 145, 145 and 80 |
| I.R. spectrum (KBr) peaks at cm$^{-1}$ | 3420,2970,2930, 1720,1685,1620, 1595,1455,1420, 1385,1360,1290, 1240,1220,1160, 1125,1095,1070, 1040,1020, 995, 890, 860, 820, 795, 785, 770 | 3420,2960,2920, 1715,1620,1590, 1525,1450,1420, 1385,1360,1290, 1240,1215,1195, 1150,1125,1090, 1070,1035, 995, 955, 950, 820, 790, 765 |
| Molecular weight: m/z by FAB-mass spectrometry | 810 (MH$^+$) | 798 (MH$^+$) |
| Molecular formula | $C_{40}H_{47}N_3O_{15}$ | $C_{38}H_{43}N_3O_{14}S$ |

TABLE 2

$^1$H-NMR spectra of FCE 24366 and FCE 24367 (200 MHz; DMSO-d$_6$; 22° C.)

| FCE 24366$^{(a)}$ | FCE 22367$^{(a)}$ |
|---|---|
| 0.96(d, J=4.8Hz, 3H, CH$_3$-7″) | 0.99(d, J=5.0Hz, 3H, CH$_3$-7) |
| 1.08(d, J=6.7Hz, 3H CH$_3$-4″) | 1.06(d, J=6.5Hz, 3H, CH$_3$-4″) |
| 1.15(d, J=6.6Hz, 3H, CH$_3$-6′) | 1.14(d, J=6.5Hz, 3H, CH$_3$-6′) |
| 1.7–1.9(m, 4H, CH$_2$-2′, CH$_2$-2″) | 1.7–1.9(m, 4H, CH$_2$-2′, CH$_2$-2″) |
| 2.09(m, 2H, CH$_2$-8) | 2.1–2.3(m, 2H, CH$_2$-8) |
| 2.22(s, 3H, CH$_3$-14) | 2.20(s, 3H, CH$_3$-14) |
| 2.97(s, 6H, N—CH$_3$-1‴, N—CH$_3$-3‴) | |
| 2.9–3.0(m, 2H, CH$_2$-10) | 2.84–3.03(two d, J=18.0Hz, 2H, CH$_2$-10) |
| 3.3–3.4(m, 1H, H-3′) | 3.40(m, 1H, H-3′) |
| 3.75(m, 1H, H-3″) | 3.75(m, 1H, H-3″) |
| 3.94(s, 3H, OCH$_3$-4) | 3.95(s, 3H, OCH$_3$-4) |
| 4.14(qd, J=6.6, <1Hz, 1H, H-5′) | 4.08(qd, J=6.5, <1Hz, 1H, H-5′) |
| 4.47(bd, J=11.1Hz, 1H, H-6″) | 4.31(d, J=10.7Hz, 1H, H-6″) |
| 4.54(d, J=4.3Hz, 1H, OH-3″) | 4.56(d, J=5.0Hz, 1H, OH-3″) |
| 4.74(m, 1H, H-4′) | 4.70(m, 1H, H-4′) |
| 4.80(m, 1H, H-1″) | 4.80(m, 1H, H-1″) |
| 4.88(m, 1H, H-7) | 4.89(m, 1H, H-7) |
| 5.06(qd, J=4.8, 11.1Hz, 1H, H-5‴) | 4.95(m, 1H, H-5″) |
| 5.20(m, 1H, H-1′) | 5.22(m, 1H, H-1′) |
| 5.46(s, 1H, OH-9) | 5.68(s, 1H, OH-9) |
| 7.6–7.9(m, 3H, H-1, H-2, H-3) | 7.6–7.9(m, 3H, H-1, H-2, H-3) |
| 8.38, 7.45(two bs, each integrating for 0.5H, enol of H-5‴) | |
| 13.18(bs, 1H, OH-11) | 13.20(bs, 1H, OH-11) |
| 13.97(bs, 1H, OH-6) | 14.0(bs, 1H, OH-6) |

$^{(a)}$Chemical shifts are expressed as δ values (ppm) with respect to tetramethylsilane.

TABLE 3

$^{13}$C-NMR spectrum of FCE 24366 (50 MHz, DMSO-d$_6$)$^a$

| | | | | | |
|---|---|---|---|---|---|
| 16.57 | C-6′ | 60.16 | C-6″ | 119.75 | C-4a |
| 20.97 | C-7″ | 62.61 | C-3″ | 134.48 | C-12a, C-10a, C-6a |
| 23.82 | C-14, C-4″ | 64.37 | C-5′ | 135.06 | |
| 23.87 | | 70.87 | C-7 | 136.05 | C-2 |

TABLE 3-continued

13C-NMR spectrum of FCE 24366 (50 MHz, DMSO-d6)[a]

| | | | | | |
|---|---|---|---|---|---|
| 26.70 | } N—CH3-1''', N—CH3-3''' | 73.57 | C-5'' | 152.44 | C-2''' |
| 27.09 | | 74.61 | C-4' | 154.25 | C-11 |
| 28.96 | C-2' | 75.01 | C-9 | 155.94 | C-6 |
| 31.39 | C-10 | 76.46 | C-5''' | 160.60 | C-4 |
| 36.25 | C-8 | 99.46 | C-1' | 162.63 | } C-4''', C-6''' |
| 44.61 | C-2'' | 106.08 | C-1'' | 163.29 | |
| 49.27 | C-3' | 110.58 | C-5a, C11a | 186.26 | C-5, C-12 |
| 56.44 | OCH3-4 | 118.78 | C-1 | 211.61 | C-13 |
| | | 119.46 | C-3 | | |

[a]As in Table 2

Structure Elucidation

Mild acid hydrolysis of both FCE 24366 and FCE 24367 give daunorubicin (III), which has been identified by direct comparison (TLC, IR, UV, NMR, mixed melting point) with an authentic sample. Hydrogenolysis of both FCE 24366 and FCE 24367 gives 7-deoxydaunomycinone (IV) identified by direct comparison with an authentic sample. Degradation products and spectroscopic data suggest that the new anthracyclines are daunomycinone glycosides in which a daunosamine containing trisaccharide-like moiety is linked to a 1,3-N,N-dimethylbarbituric acid unit for FCE 24366 (I) and to a 2-thiobarbituric acid unit for FCE 24367 (II).

The proposed structure of FCE 24366 (I) and FCE 24367 (II) are shown in Scheme 1 below:

Biological Activity (a) Antibacterial activity

The in vitro minimum inhibitory concentration (MIC) of FCE 24366, FCE 24367 and daunorubicin, determined for some microorganism using the standard tube dilution procedure, are reported in Table 4.

(b) Antitumor activity

The cytotoxic activity of the new anthracyclines, FCE 24366 and FCE 24367 have been tested in vitro on cultured HeLa cells, and P388 leukemia cells sensitive (P 388/S) or resistant (P 388/R) to doxorubicin. As shown in Table 5 both FCE 24366 and FCE 24367 were found cytotoxic for HeLa and P 388/S cell lines at dosage levels several times lower than those of daunorubicin, and furthermore the new anthracyclines show high activity on P 388/R cell line which is cross-resistant to most anthracyclines.

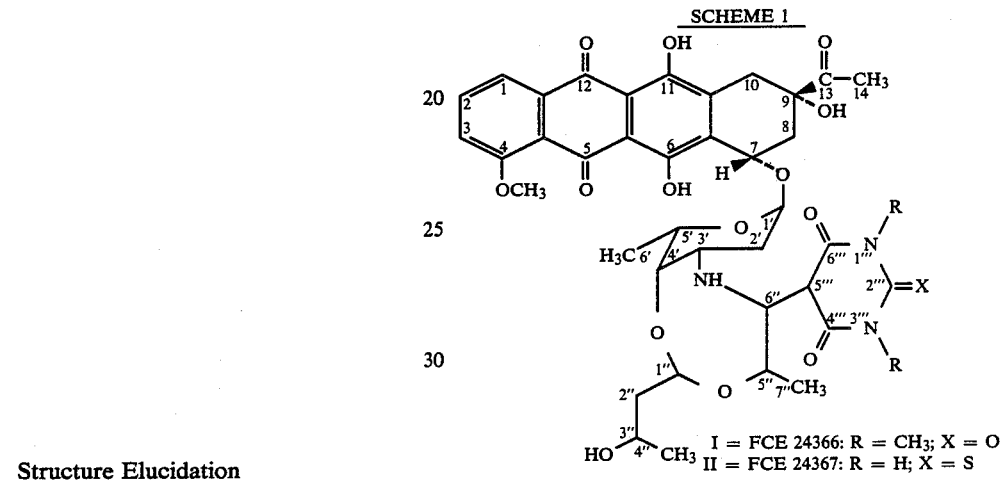

SCHEME 1

I = FCE 24366: R = CH3; X = O
II = FCE 24367: R = H; X = S

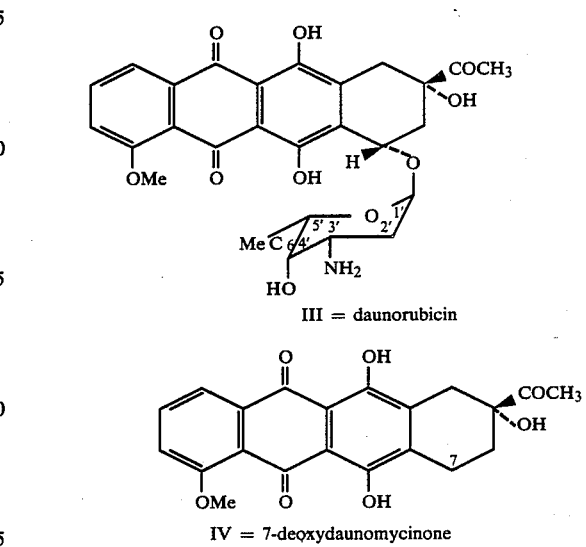

III = daunorubicin

IV = 7-deoxydaunomycinone

TABLE 4

Antibacterial Activity of FCE 24366 and FCE 24367

| | MIC in μg/ml | | |
|---|---|---|---|
| Test Organism | Daunorubicin | FCE 24366 | FCE 24367 |
| *Staphylococcus aureus* 209P | 6.25 | 0.78 | 6.25 |
| *Staphylococcus aureus* 153 | 25 | 0.78 | 6.25 |
| *Sarcina lutea* ATCC 9341 | 1.56 | 0.19 | 0.78 |
| *Streptococcus pyogenes* ATCC 12384 | 3.12 | 3.12 | 6.25 |
| *Streptococcus faecalis* ATCC 8043 | >100 | 12.5 | 100 |
| *Klebeiella pneumoniae* ATCC 10031 | >100 | 0.78 | 25 |
| *Escherichia coli* ATCC 11303 | 3.12 | 0.39 | 3.12 |
| *Escherichia coli* 026B6 | 6.25 | 1.56 | 12.5 |

TABLE 4-continued

Antibacterial Activity of FCE 24366 and FCE 24367

| | MIC in µg/ml | | |
|---|---|---|---|
| Test Organism | Daunorubicin | FCE 24366 | FCE 24367 |
| *Proteus morganii* ATCC 25830 | >100 | 12.5 | 100 |

TABLE 5

Cytotoxicity of FCE 24366 and FCE 24367

| | $ID_{50}$ (ng/ml) | | |
|---|---|---|---|
| Compound | HeLa[a] | P388/S[b] | P388/R[b] |
| FCE 24366 (I) | 0.09 | 0.036 | 1.2 |
| FCE 24367 (II) | 0.7 | 0.003 | 3.8 |
| Daunorubicin (III) | 19 | 9.5 | 750 |

[a]Cells are exposed to the drugs for 24 hr then plated
[b]Cells are exposed to the drugs for 48 hr then plated When tested "in vivo" against P388 ascitic leukemia in mice, as reported in Table 6, both FCE 24366 and FCE 24367 were found at dosage levels several times lower (1/100 to 1/10) as active as daunorubicin (III).

Against Gross leukemia FCE 24366 displayed an activity comparable with that of daunorubicin at remarkably lower dosages, as shown in Table 7.

TABLE 6

Activity against P388 ascitic leukemia in mice[a]

| Compound | Dose (mg/Kg)[b] | MST (T/C %)[c] | Toxic deaths[d] |
|---|---|---|---|
| FCE 24366 (I) | 0.012 | 130 | 0/10 |
| | 0.025 | 135 | 0/10 |
| | 0.05 | 150 | 0/10 |
| | 0.1 | 165 | 1/10 |
| FCE 24367 (III) | 0.3 | 145 | 0/10 |
| | 0.45 | 150 | 1/10 |
| | 0.68 | 155 | 1/10 |
| Daunorubicin (II) | 2.9 | 160 | 0/10 |
| | 4.4 | 150 | 7/10 |

[a]Mice were treated i.p. on day 1 after tumor cell inoculation.
[b]Injected as 1:9 Tween 80:water suspension.
[c]Median survival time expressed as percentage of untreated controls.
[d]Evaluated on the basis of macroscopic autopic findings.

TABLE 7

Activity against Gross leukemia in mice[a]

| Compound | Dose (mg/Kg)[b] | MST (T/C %)[c] | Toxic deaths[d] |
|---|---|---|---|
| FCE 24366 (I) | 0.13 | 117 | 0/9 |
| | 0.20 | 192 | 0/8 |
| | 0.30 | 150 | 2/9 |
| Daunorubicin (III) | 10 | 183 | 0/9 |
| | 15 | 217 | 0/9 |
| | 22.5 | 83 | 9/9 |

[a]Mice were treated i.v. on day 1 after tumor cell i.v. inoculation.
[b]Injected as 1:9 Tween 80:water suspension
[c]Median survival time expressed as percentage of untreated controls.
[d]Evaluated on the basis of macroscopic autoptic findings.

The following examples serve to illustrate the invention without limiting it.

EXAMPLE 1

A culture of *Streptomyces peucetius* strain ATCC 29050 has been grown for 14 days at 28° C. on agar slants of the following maintenance medium (medium SA).

Glucose, 3%; brewer's dry yeast, 1.2%; NaCl, 0.1%; $KH_2PO_4$, 0.05%; $CaCO_3$, 0.1%; $MgSO_4$, 0.005%; $FeSO_4.7H_2O$, 0.0005%; $ZnSO_4.7H_2O$, 0.0005%; $CuSO_4.5H_2O$, 0.0005%; agar, 2%; tap water up to 100 ml; pH 6.7; sterilization is carried out by heating in an autoclave at 115° C. for 20 minutes. The spores of the culture so obtained are collected and suspended in 3 ml of sterile distilled water; the suspension so obtained is inoculated in 300 ml Erlenmeyer flasks containing 60 ml of the following liquid growth medium: brewer dry yeast 0.3%; peptone 0.5%; $Ca(NO_3)_2.4H_2O$ 0.05%; tap water up to 100 ml. Sterilization by heating in autoclave at 120° C. for 20 minutes. The pH value of this medium after sterilization is between 6.8 and 7.0. The inoculated flasks are shaken for 2 days at a temperature of 28° C. on a rotary shaker running at 250 rpm and describing a circle of 7 cm in diameter. 1.5 ml of the culture grown as described above are inoculated in a 300 ml Erlenmeyer flask containing 50 ml of the following production medium: glucose 6%; brewer's dry yeast 3%; NaCl 0.2%; $KH_2PO_4$ 0.1%; $CaCO_3$ 0.2%; MgS 0.01%; $FeSO_4.7H_2O$ 0.001%; $ZnSO_4.7H_2O$ 0.001%; $CuSO_4.H_2O$ 0.001%; tap water up to 100 ml, pH 6.7. Sterilization by heating in autoclave at 115° C. for 20 minutes.

The flasks are thus incubated at 28° C. for 7 days under the same conditions described for the seed phase.

At the 48th hour of fermentation an addition of 5% sodium 1,3-N,N-dimethyl barbiturate suspension in distilled water is made to each flask at a final concentration of 4 g/l.

The maximum concentration of the active compound is reached in the 6-7th day of fermentation with production of 20 mcg/ml of FCE 24366.

EXAMPLE 2

The whole fermentation procedure is carried out as described for example 1, the only difference being the time of the sodium 1,3-N,N-dimethyl barbiturate addition which is made at 72 hrs of fermentation.

The maximum concentration of FCE 24366 is reached in the 6-7th day of fermentation with a production of 30 mcg/ml.

EXAMPLE 3

The whole fermentation procedure is carried out as described for example 1, the only difference being the utilization of a different microorganism which in this case is *Streptomyces peucetius*, var. carneus, strain ATCC 21354.

The maximum concentration of FCE 24366 is reached in the 6-7th day of fermentation with a production of 20 mcg/ml.

EXAMPLE 4

The whole fermentation procedure is carried out as described for example 1, the only difference being the utilization of a different microorganism which in this case is *Streptomyces peucetius* var. caesius, strain ATCC 27952.

The maximum concentration of FCE 24366 is reached in the 6-7th day of fermentation with a production of 30 mcg/ml.

EXAMPLE 5

The whole fermentation procedure is carried out as described for example 1, the only difference being the utilization of a different microorganism which in this case is *Streptomyces peucetius* var. carminatus, strain ATCC 31502.

The maximum concentration of FCE 24366 is reached in the 6-7th day of fermentation with a production of 25 mcg/ml.

EXAMPLE 6

The whole fermentation procedure is carried out as described for example 1, the only difference being the addition of sodium 2-thiobarbiturate.

The maximum concentration of FCE 24367 is reached in the 6-7th day of the fermentation with a production of 30 mcg/ml.

EXAMPLE 7

The whole fermentation procedure is carried out as described for example 1, but using *Streptomyces peucetius*, var. carneus, strain ATCC 21354 instead of strain ATCC 29050 and sodium 2-thiobarbiturate instead of sodium 1,3-N,N-dimethyl barbiturate.

The maximum concentration of FCE 24367 is reached in the 6-7th day of fermentation with a production of 25 mcg/ml.

EXAMPLE 8

The whole fermentation procedure is carried out as described for example 1, but using *Streptomyces peucetius*, var. caesius, strain ATCC 27952 instead of strain ATCC 29050 and sodium 2-thiobarbiturate instead of sodium 1,3-N,N-dimethyl barbiturate.

The maximum concentration of FCE 24367 is reached in 6-7th day of fermentation with a production of 40 mcg/ml

EXAMPLE 9

The whole fermentation procedure is carried out as described for example 1, but using *Streptomyces peucetius*, var. carminatus, strain ATCC 31502 instead of strain 29050 and sodium 2-thiobarbiturate instead of sodium 1,3-N,N-dimethyl barbiturate.

The maximum concentration of FCE 24367 is reached in 6-7th day of fermentation with a production of 30 mcg/ml.

EXAMPLE 10

A culture of *Streptomyces peucetius* var, caesius, strain ATCC 27952 is obtained according to the procedure described in example 1.

The spores of three slants are pooled and collected in 10 ml of sterile distilled water; the suspension so obtained is inoculated in a 2 l baffled round-bottomed flask containing 500 ml of the seed medium described in example 1. The flask is incubated for 48 hours on a rotary shaker running at 120 rpm and describing a circle of 70 mm diameter, at a temperature of 28° C. The whole seed is inoculated in an 80 l stainless-steel fermenter containing 50 l of production medium described in example 1, and sterilized by vapour at 120° C. for 30 minutes. After 72 hours of fermentation, an addition of sodium 1,3-N,N-dimethyl barbiturate at a final concentration of 4 g/l is made. The fermentation is carried out at 28° C., stirred at 230 rpm and aereated with an air flow of 0.7 liter/liter of the medium/minute.

The maximum concentration of FCE 24366 is reached in the 6-7th day of fermentation with a production of 30 mcg/ml.

EXAMPLE 11

The whole fermentation procedure is carried out as described for example 10, the only difference being the addition of sodium 2-thiobarbiturate. The maximum concentration of FCE 24367 is reached in the 6-7th day of fermentation with a production of 30 mcg/ml.

EXAMPLE 12

The whole beer (4 l) from a fermentation, obtained according to example 1 was filtered at pH 7.5 using 3% diatomaceus earth as filter aid. The wet filter cake was extracted with acetone (4 l). After filtration two additional extractions with acetone (respectively with 3 and 2 l) were effected to ensure a complete recovery of the red pigments. The combined acetone extracts were concentrated under reduced pressure and the concentrate (1 l) was extracted at pH 7.5 with ethyl acetate. The organic extracts (3 l) were combined, dried with anhydrous sodium sulphate and concentrated under reduced pressure to a small volume (50 ml). By addition of n-hexane (200 ml) FCE 24366 was obtained in crude form as brown purple powder (0.1 g).

EXAMPLE 13

A solution of crude FCE 24366 (0.1 g), obtained according to example 12, in a 7:3:3 chloroform:methanol:toluene mixture, was chromatographed on a silica gel dry column using the above mentioned mixture as eluting solvent. Selected fractions, monitored by TLC, were concentrated under reduced pressure to small volume. Addition of a fivefold volume of n-hexane gave pure FCE 24366 (0.05 g), that after crystallization from ethyl acetate was obtained as fine red needles: m.p. 195°-196° C. (with decomposition).

EXAMPLE 14

The whole beer (4 l) from a fermentation obtained according to example 6 was worked up as described in example 12. FCE 24367 was obtained in crude form as brown, purple powder (0.12 g

EXAMPLE 15

A solution of crude FCE 24367 (0.12 g), obtained according to example 14, was purified by column chromatography and crystallized, as described in example 13, to give FCE 24367 (0.06 g) as red needles: m.p. 210°-211° C. (with decomposition).

EXAMPLE 16

A solution of FCE 24366 (0.1 g) in dioxane (2 ml) and 0.1N aqueous acetic acid (2 ml) was heated for 2 hrs at 85° C. The reaction mixture, diluted with water (10 ml) and adjusted to pH 8.5 with aqueous NaHCO$_3$, was extracted with chloroform. The extract, washed with water and dried on anhydrous sodium sulphate, was concentrated under reduced pressure to a small volume. Addition of methanolic hydrogen chloride gave a red crystalline compound (0.05 g): m.p. 186°-188° C. (with decomposition), identified as daunorubicin.HCl (III) after comparison with an authentic sample.

EXAMPLE 17

From FCE 24367 (0.1 g) subjected to acid hydrolysis, as described in example 16, crystalline daunorubicin.HCl (0.05 g) was obtained.

EXAMPLE 18

A solution of FCE 24366 (0.1 g) in dioxane (10 ml) was hydrogenated in the presence of 5% palladium on barium sulphate (0.5 g) for 1 hr at room temperature. The reaction mixture was filtered, diluted with water (5 ml) and extracted with with chloroform. Concentration of the chloroform extract gave a red crystalline compound (0.03 g): m.p. 228°-230° C., identified as 7-deoxydaunomycinone (IV), after comparison with an authentic sample. The TLC analysis of the almost colourless aqueous phase indicated the presence of a single compound which, after acid hydrolysis (aqueous acetic acid for 2 hrs at 85° C.) gave a mixture of hydrolysis product among which daunosamine was identified by direct comparison with an authentic sample.

EXAMPLE 19

After hydrogenolysis of FCE 24367 (0.1 g) as described for example 18, 7-deoxydaunomycinone (0.03 g) was obtained and daunosamine was identified among the hydrolysis products of the glycosidic moiety.

We claim:

1. A anthracycline glycoside of the general formula:

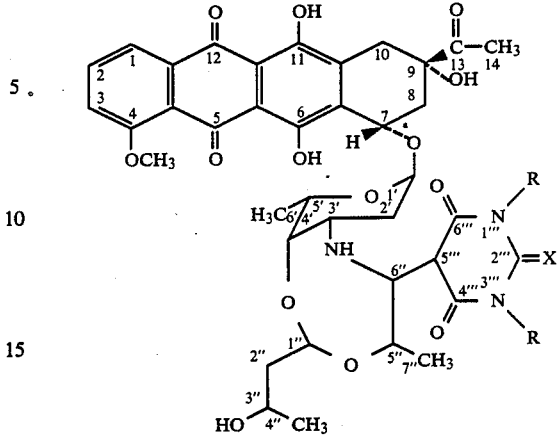

wherein R represents a methyl group and X is an oxygen atom, or R represents hydrogen and X is a sulphur atom.

2. A pharmaceutical composition comprising an anthracycline glycoside as claimed in claim 1 in an antibiotic amount effective for treatment of humans or animals in admixture with pharmaceutically acceptable diluent or carriers.

3. A pharmaceutical composition for inhibiting the growth of P 388 leukemia and Gross leukemia comprising a therapeutically effective amount of a compound as claimed in claim 1 in admixture with a pharmaceutically acceptable diluent or carrier.

* * * * *